United States Patent [19]

Iwahashi et al.

[11] Patent Number: 4,532,919

[45] Date of Patent: Aug. 6, 1985

[54] SHOULDER PATTING MEANS

[75] Inventors: Shoji Iwahashi; Ken Nakai, both of Kainan, Japan

[73] Assignee: Aisen Kogyo, Ltd., Wakayama, Japan

[21] Appl. No.: 391,269

[22] Filed: Jun. 23, 1982

[51] Int. Cl.[3] .............................................. A61N 23/00

[52] U.S. Cl. .......................................... 128/54; 128/44

[58] Field of Search ........................ 128/54, 44, 42, 55; 46/191; 81/52.3

[56] References Cited

U.S. PATENT DOCUMENTS

| | | | |
|---|---|---|---|
| 323,447 | 8/1885 | Ruebsam | 128/54 |
| 1,267,554 | 5/1918 | Karatsu | 128/54 |
| 1,478,388 | 12/1923 | Gray | 128/54 |
| 1,649,089 | 11/1927 | Volckening | 128/54 |
| 1,915,190 | 6/1933 | Koment | 128/54 |
| 1,973,768 | 9/1934 | Knapp | 128/54 |

FOREIGN PATENT DOCUMENTS

| | | | |
|---|---|---|---|
| 122995 | 11/1900 | Fed. Rep. of Germany | 128/55 |
| 222208 | 12/1909 | Fed. Rep. of Germany | 128/54 |
| 476466 | 2/1927 | Fed. Rep. of Germany | 128/54 |
| 684389 | 12/1952 | United Kingdom | 128/55 |

*Primary Examiner*—Richard J. Apley
*Assistant Examiner*—Harry Macey
*Attorney, Agent, or Firm*—Edwin E. Greigg

[57] ABSTRACT

Shoulder patting device comprising a grip stick, two resilient plates which extend from one end of the grip stick in the form of Y-shape and first and second tip members which are respectively secured to the tips of the resilient plates.

3 Claims, 4 Drawing Figures

Fig. 1
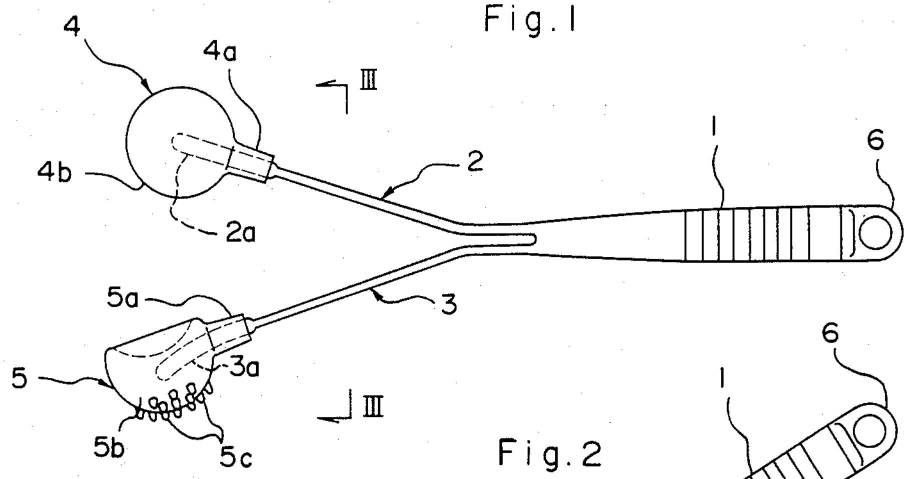
Fig. 2
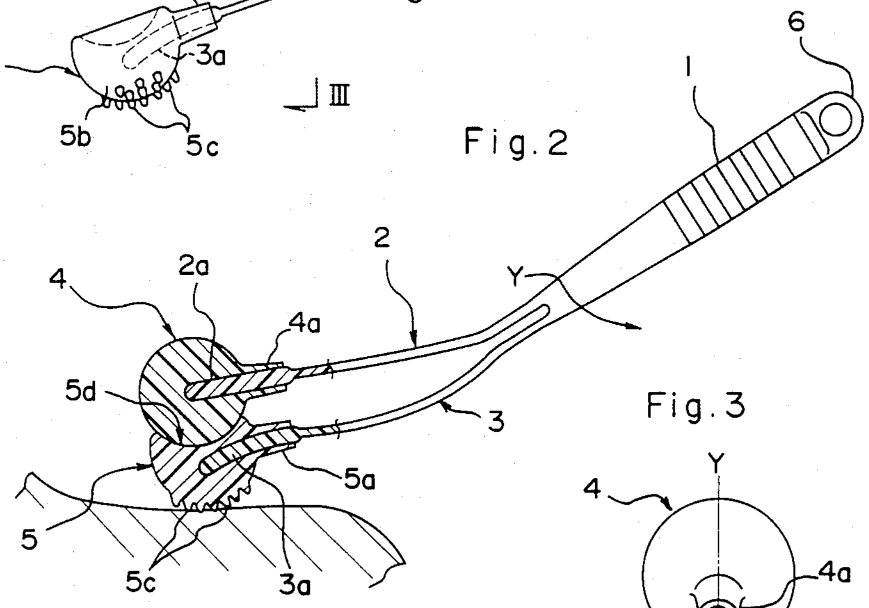
Fig. 3
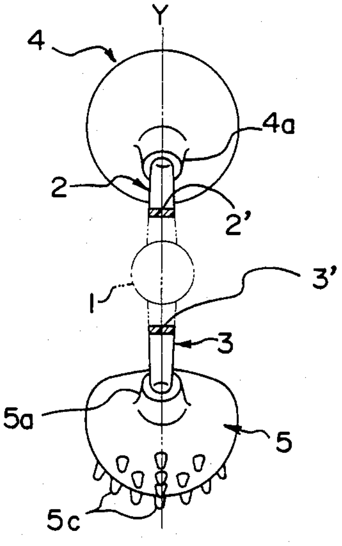
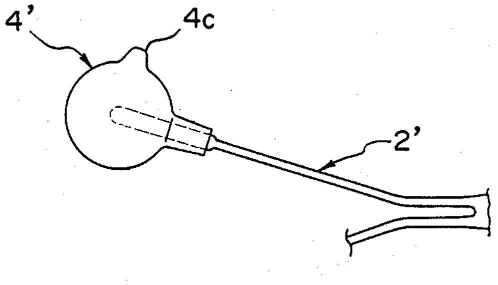
Fig. 4

SHOULDER PATTING MEANS

BACKGROUND OF THE INVENTION (1) Field of the Invention

The present invention relates to shoulder patting means with which one can pat himself on the shoulders or the like.

(2) Description of the Prior Art

There is conventionally known such shoulder patting means of the manually operated type in which a small mallet is attached to a back scratcher, i.e., a rod member provided at the tip thereof with scratching means, or a stick is connected to a coil spring to the tip of which a resilient ball is attached. Such conventional shoulder patting means has only one shoulder patting member such as a small mallet or a resilient ball.

As an effective massage method, there is practised a so-called two-stage patting according to which, with the palms faced to each other, the both hands are clasped each other while providing a space therebetween, and such hands are simultaneously brought down on the shoulders. According to such two-stage patting, immediately after the lower hand strikes the shoulder, the upper hand strikes the lower hand. The first strike is a mere massage in which a strike force is applied directly to the shoulder, while the second strike is transmitted to the shoulder through the lower hand as a cushion. Namely, the second strike may produce an effect similar to that obtained by a so-called finger-pressure treatment to be made with the hand pressingly applied to the body. It is known that a series of such two different actions which are continuously performed, produce comfortable vibration on the shoulder, thereby to relieve the stiffness in the shoulders more effectively than a simple single strike action.

However, it is not possible to obtain such two-stage patting effect with a conventional shoulder patting means having only one shoulder patting member.

In view of the foregoing, it has been long desired to develop shoulder patting means having such two-stage patting effect.

SUMMARY OF THE INVENTION

It is an object of the present invention to provide novel shoulder patting means capable of mechanically performing such two-stage patting as mentioned earlier.

Shoulder patting means in accordance with the present invention comprises: a grip stick; two resilient plates having the substantially same length extending from one end of the grip stick to form a Y shape together with the grip stick, the wider surfaces of these plates being located at right angles to the swing direction of the grip stick and overlapping each other with a distance provided therebetween in the swing direction of the grip stick; and first and second tip members respectively secured to the tips of the resilient plates.

When the shoulder patting means having two shoulder patting members of the present invention is brought down on the shoulder, the first tip member as one shoulder patting member strikes the shoulder, and, with the first tip member applied to the shoulder, the second tip member as the other shoulder patting member then strikes the first tip member, such second strike being transmitted to the shoulder through the first tip member as a cushion.

The second strike action produces an effect similar to that obtained by a finger-pressure treatment. Thus, each combined strike action may relieve the stiffness in the shoulders more effectively than shoulder patting performed by a single strike action.

It is further pointed out that, immediately after the first strike directly acting on the shoulder, the second strike indirectly acting on the shoulder is made, thus producing comfortable vibration on the shoulder. Thus, there can be mechanically realized a so-called two-stage shoulder patting capable of effectively relieving the stiffness in the shoulder.

Other advantages will be apparent from the following description.

BRIEF DESCRIPTION OF THE DRAWINGS

The invention will be further discussed, by way of example, with reference to the accompanying drawings, in which:

FIG. 1 is a front view of a first embodiment of shoulder patting means in accordance with the present invention, illustrating the state where it is not operated;

FIG. 2 is a front view, with portions broken away, of the shoulder patting means in accordance with the present invention, illustrating the state where it strikes the shoulder;

FIG. 3 is a section view taken along the line III—III in FIG. 1; and

FIG. 4 is a front view of main portions of a second embodiment of the shoulder patting means in accordance with the present invention.

DETAILED DESCRIPTION OF THE PREFERRED EMBODIMENTS

As shown in FIG. 1, a grip stick 1 made of hard nylon has two band-shape resilient plates 2 and 3 extending from the tip of the grip stick 1 so as to form a Y shape together with the grip stick 1. As shown in FIG. 3, these resilient plates 2 and 3 are arranged such that the width of the plate surfaces 2′ and 3′ thereof are perpendicular to the swing direction Y of the grip stick 1 and overlap each other with a converging spacing provided therebetween in the swing direction Y which separates the two plates from each other.

The lower resilient plate 3 has at the tip thereof a first tip member 5 made of polyethylene, while the upper resilient plate 2 has at the tip thereof a second tip member 4 made of polyethylene softer than the polyethylene constituting the first tip member 5.

The second tip member 4 is formed in a spherical shape and has a projecting sleeve 4*a*. The first tip member 5 is formed in a semi-spherical shape and has an upper concave surface 5*d* curved with curvature substantially same as that of the lower spherical portion 4*b* of the second tip member 4. The first tip member 5 has an integrally projecting sleeve 5*a* and a plurality of projections 5*c* attached to the lower spherical portion 5*b*.

These tip members 4 and 5 are respectively attached to the upper and lower resilient plates 2 and 3 by inserting the tip rod portions 2*a* and 3*a* of the resilient plates 2 and 3 into the sleeves 4*a* and 5*a* so as to be embeded in the tip members 4 and 5. The resilient plates 2 and 3 have the substantially same length.

In FIG. 1 illustrating the shoulder patting means in the state where it is not brought down on the shoulder, the resilient plates 2 and 3 present a Y shape together with the grip stick 1 such that a suitable distance is provided between the first tip member 5 and the second tip member 4.

The resilient members 2 and 3 have such resiliency that the first tip member 5 and the second tip member 4 come into collision with each other as shown in FIG. 2 due to resilient deformation of the resilient plates 2 and 3 when the first tip member 5 strikes the shoulder.

The description hereinafter will discuss the operation of the shoulder patting means in accordance with the present invention.

Before the grip stick 1 held with one hand is brought down on the shoulder, the first and second tip members 4 and 5 are separated from each other as shown in FIG. 1. When the grip stick 1 is brought down on the shoulder, the first tip member 5 of the resilient plate 3 first strikes the shoulder, and the second tip member 4 attached to the resilient plate 2 having a length substantially same as that of the resilient plate 3, then immediately strikes the first tip member 5. At this time, the first tip member 5 remains as applied onto the shoulder as shown in FIG. 2, since the resilient plate 3 integral with the first tip member 5 is resiliently deformed. In such state, the second tip member 4 comes into collision with the substantially center portion of the first tip member 5 with the upper concave surface 5*d* of the first tip member 5 being as a guide. The strike of the second tip member 4 is transmitted to the shoulder through the first tip member 5 as a cushion. This second strike may produce an effect similar to that produced by a finger-pressure treatment.

Then, when the grip stick 1 is brought up, the first and second tip members 5 and 4 are separated from each other and returned to the original state as shown in FIG. 1 by resiliency of the resilient plates 2 and 3. There is thus produced on the shoulder comfortable vibration by the combination of the first strike directly acting on the shoulder with the second indirect strike having a cushion effect made immediately after the first strike.

Even if the first and second tip members 5 and 4 are positionally shifted when the second tip member 4 strikes the first tip member 5, that portion of the second tip member 4 which strikes the first tip member 5, undergoes no change in shape, since the second tip member 4 is formed in a spherical shape. Thus, an effective strike action may be provided.

FIG. 4 shows a second embodiment of the present invention.

In this embodiment, the second tip member 4' of spherical shape has on the upper portion thereof one projection 4*c* in the swing direction of the resilient plate 2'. When the shoulder patting means shown in FIG. 4 is brought down on the shoulder with the second tip member 4' turned down, the shoulder patting surface is smaller than that of the first embodiment having a plurality of projections 5*c* on the first tip member 5. Thus, a larger surface pressure may be provided, thereby to advantageously produce a stronger excitation.

We claim:

1. A shoulder patting means comprising:
   - a grip stick having one free end;
   - first and second resilient plates having substantially the same length and width extending from one end of said grip stick forming a one-piece, integral construction therewith and spaced from each other to form a Y-shape with said resilient plates normally diverging from each other in a direction away from said grip stick, said resilient plates being disposed in spaced relation with their width perpendicular to a swing direction of said grip stick, first and second tip members respectively secured to respective ends of said first and second resilient plates;
   - said first tip member formed of a truncated sphere with upper and lower portions, said upper portion being truncated with an upper surface parallel with said length of said first resilient plate and provided with a concave depression within said sphere for reception therein intermittently of said second tip member, said lower portion of said first tip member comprising substantially a hemisphere serving as a shoulder contacting surface when in use,
   - said second tip member having a substantially spherical configuration with a radius of curvature providing a complemental mating surface to that of said concave depression in said first tip member, both of said tip members being formed of an elastic material, said second tip member having a softer surface than that of said first tip member;
   - whereby a vibratory beating effect is conveyed to a user's body when said grip stick is swung in a direction such that the width of said first and second resilient plates are parallel with the user's body.

2. Shoulder patting means as set forth in claim 1, wherein said lower portion of the first tip member is provided with a plurality of projections.

3. Shoulder patting means as set forth in claim 2, wherein the second tip member has on the upper surface thereof one projection.

* * * * *